(12) United States Patent
Waki (10) Patent No.: US 9,402,600 B2
(45) Date of Patent: Aug. 2, 2016

(54) 3-DIMENSIONAL ELASTIC IMAGE GENERATION METHOD AND ULTRASONIC DIAGNOSTIC APPARATUS

(75) Inventor: Koji Waki, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 208 days.

(21) Appl. No.: 13/817,662

(22) PCT Filed: Jul. 28, 2011

(86) PCT No.: PCT/JP2011/067188
§ 371 (c)(1),
(2), (4) Date: Feb. 19, 2013

(87) PCT Pub. No.: WO2012/029458
PCT Pub. Date: Mar. 8, 2012

(65) Prior Publication Data
US 2013/0150720 A1 Jun. 13, 2013

(30) Foreign Application Priority Data
Aug. 31, 2010 (JP) .................................. 2010-194183

(51) Int. Cl.
*A61B 8/08* (2006.01)
*G01S 7/52* (2006.01)
*G01S 15/89* (2006.01)

(52) U.S. Cl.
CPC . *A61B 8/52* (2013.01); *A61B 8/485* (2013.01); *G01S 7/52042* (2013.01); *G01S 15/8993* (2013.01); *A61B 8/5269* (2013.01); *G01S 7/52077* (2013.01)

(58) Field of Classification Search
CPC ........ A61B 8/485; A61B 8/52; A61B 8/5269; G01S 7/52042; G01S 7/52077; G01S 15/8993
See application file for complete search history.

(56) References Cited

U.S. PATENT DOCUMENTS

| 6,511,426 B1 * | 1/2003 | Hossack et al. ............... 600/437 |
| 2003/0023910 A1 * | 1/2003 | Myler .................. H04N 17/004 714/704 |

(Continued)

FOREIGN PATENT DOCUMENTS

| CN | 102481145 A | 5/2012 |
| JP | A-2006-271594 | 10/2006 |
| JP | A-2008-259555 | 10/2008 |

(Continued)

OTHER PUBLICATIONS

International Search Report issued in Application No. PCT/JP2011/067188; Dated Sep. 20, 2011 (With Translation).
Chinese Office Action issued in Chinese Patent Application No. 201180031496.3 on May 20, 2014.

*Primary Examiner* — Long V Le
*Assistant Examiner* — Colin T Sakamoto
(74) *Attorney, Agent, or Firm* — Oliff PLC (57) ABSTRACT

In order to improve the continuity of the image qualities in the minor-axis direction of plural sets of elastic frame data that constitute elastic volume data and generate a high-quality 3-dimensional elastic image, regarding each elastic frame data constituting elastic volume data, a noise frame interpolation unit subjects plural sets of elastic frame data including said elastic frame data and adjacent in a swing direction to synthesis processing, generates the elastic volume data from the synthesized plural sets of elastic frame data, and volume renders the elastic volume data to generate a 3-dimensional elastic image. The noise frame interpolation unit stores plural sets of elastic volume data, subjects plural sets of elastic frame data at corresponding swing angle positions among the stored plural sets of elastic volume data to synthesis processing to generate synthetic elastic frame data and elastic volume data from the synthesized plural sets of elastic frame data.

9 Claims, 9 Drawing Sheets

(56) References Cited

U.S. PATENT DOCUMENTS

2011/0160590 A1 6/2011 Waki et al.
2012/0157831 A1 6/2012 Waki

FOREIGN PATENT DOCUMENTS

| JP | A-2010-115372 | 5/2010 |
| WO | WO 2010/024023 A1 | 3/2010 |

* cited by examiner

3-DIMENSIONAL ELASTIC IMAGE GENERATION METHOD AND ULTRASONIC DIAGNOSTIC APPARATUS

FIELD OF THE INVENTION

The present invention relates to a 3-dimensional elastic image generation method for displaying a 3-dimensional elastic image showing the hardness or softness of biological tissue in an object to be examined using ultrasonic waves and an ultrasonic diagnostic apparatus by which the method is carried out.

DESCRIPTION OF RELATED ART

An ultrasonic diagnostic apparatus is capable of transmitting ultrasonic waves to an object by an ultrasonic probe and receiving the reflected echo signals returned from the biological tissue inside of the object, so as to generate an ultrasonic image such as a 3-dimensional tomographic image and a 3-dimensional elastic image on the basis of the received signals and display the generated image on a monitor for making diagnosis.

On the other hand, quality improvement of ultrasonic images such as improvement of the resolution or noise reduction has been demanded for advancement of accuracy in diagnosis.

For example, Patent Document 1 proposes a technique which extracts the 2-dimensional elastic frames having the same pressing amount (displacement) from the plural sets of 2-dimensional elastic frame data that are consecutively acquired to form elastic volume data and constructs a high quality 3-dimensional elastic image by volume rendering the formed elastic volume data. The same document also proposes a technique for constructing a high quality 3-dimensional elastic image by synthesizing elastic volume data sets using only the 2-dimensional elastic frames having high correlation coefficient in place of displacement or pressure.

PRIOR ART DOCUMENTS

Patent Documents

Patent Document 1: JP-A-2008-259555

SUMMARY OF INVENTION

Technical Problem

However, though the technique disclosed in Patent Document 1 is capable of constructing a high-quality 3-dimensional elastic image in a certain aspect, since of image quality in the array direction (hereinafter referred to as the minor-axis direction) of the plural sets of elastic frame data that form elastic volume data is not considered, generation of noise in 3-dimensional elastic images still remains as a problem. Also, construction of high quality 3-dimensional elastic images in real time is not considered in the above-mentioned technique.

The objective of the present invention is to establish the 3-dimensional elastic image generation method capable of stably generating high quality 3-dimensional elastic images by improving the continuity of image quality in the minor-axis direction of the plural sets of elastic frame data that form the elastic volume data.

BRIEF SUMMARY OF THE INVENTION

In order to achieve the above-described objective, a first example of the present invention, in the 3-dimensional elastic image generation method for generating 3-dimensional elastic images by volume rendering based on elastic volume data formed by the plural sets of elastic frame data acquired from an object and in the respective elastic frame data sets that form the elastic volume data, synthesizes the plural sets of elastic frame data that are adjacent in the swing direction including the relevant elastic frame data, generates elastic volume data using the synthesized plural sets of elastic frame data, and generates the 3-dimensional elastic image by volume rendering the elastic volume data.

The present invention has its characteristics in the generation method of elastic volume data. That is, generation of elastic volume data is executed by replacing each set of elastic frame data which forms elastic volume data with synthetic elastic frame data in which adjacent plural sets of elastic frame data are synthesized. In this manner, synthetic elastic frame data sets that form elastic volume data become averaged data of adjacent plural elastic frame data. Moreover, since adjacent plural sets of elastic frame data are also averaged data of the adjacent plural sets of elastic frame data respectively in the same manner, the continuity can be improved in image quality of the plural sets of elastic frame data that form elastic volume data in the minor-axis direction. For example, even when a noise is included in one piece of elastic frame data, the noise can be suppressed by synthesizing adjacent plural sets of elastic frame data of high quality. In other words, it is possible to construct volume data having high continuity by removing the influence of noise, even in the case that the continuity is lost in the minor-axis direction at the time of creating volume data due to the influence of noise frame.

Effect of the Invention

In accordance with the present invention, the continuity of image quality can be improved in the minor-axis direction of the plural sets of elastic frame data that form elastic volume data, which leads to construction of high-quality 3-dimensional elastic images.

DETAILED DESCRIPTION OF THE INVENTION

Figure 1:
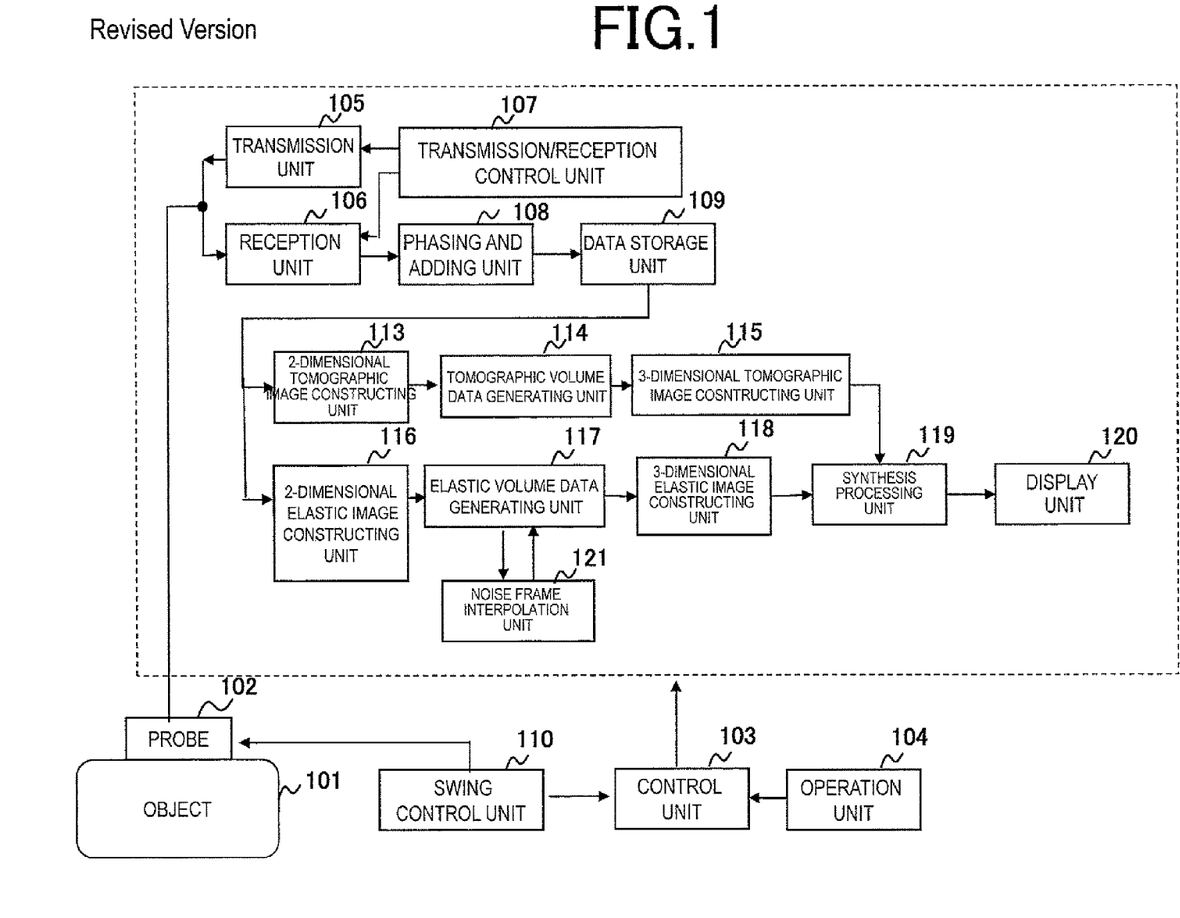
FIG. 1 is a block diagram of the general configuration in the ultrasonic diagnostic apparatus of a first example related to the present invention.

The configuration of the ultrasonic diagnostic apparatus in an example to which the 3-dimensional elastic image generation method of the present invention is applied will be described referring to FIG. 1. As shown in FIG. 1, an ultrasonic diagnostic apparatus 100 is provided with an ultrasonic probe 102 for using by applying to an object 101, a transmission unit 105 configured to repeatedly transmit ultrasonic waves to the object 101 at predetermined intervals via the ultrasonic probe 102, a reception unit 106 configured to receive the reflected echo signals reflected from the object 101, a transmission/reception control unit 107 configured to control the transmission unit 105 and the reception unit 106, and a phasing and adding unit 108 configured to perform phasing and adding of the reflected echo signals received from the reception unit 106.

The ultrasonic probe 102 is provided with plural transducers arrayed therein, and has a function to transmit and receive ultrasonic waves to and from the object 101 via the transducers. The ultrasonic probe 102 is formed by plural transducers arrayed in rectangular or fan shape, capable of 3-dimensionally transmitting and receiving ultrasonic waves by mechanically swinging the transducers in the direction orthogonal to the array direction (major-axis direction) of the plural transducers (minor-axis direction). The ultrasonic probe may also be the type in which plural transducers are 2-dimensionally arrayed to electronically control the transmission and reception of ultrasonic waves.

The transmission unit 105 generates transmission pulses for producing ultrasonic waves by driving the transducers of the ultrasonic probe 102. The transmission unit 105 has a function to set the convergence point of the transmitted ultrasonic waves at a certain depth. Also, the reception unit 106 amplifies the reflected echo signals received by the ultrasonic probe 102 at a predetermined gain and generates RF signals, i.e. reception signals. The transmission/reception control unit 107 of ultrasonic waves controls devices such as the transmission unit 105 and the reception unit 106. The phasing and adding unit 108 controls the phase of the RF signals that are amplified in the reception unit 106, and forms a reception beam of the ultrasonic waves with respect to one or plural convergent points to generate RF signal frame data (equivalent to raw data).

The ultrasonic diagnostic apparatus 100 is provided with a data storage unit 109 configured to store the RF signal frame data generated in the phasing and adding unit 108 and a 2-dimensional tomographic image construction unit 113 configured to construct a 2-dimensional tomographic image on the basis of the RF signal frame data stored in the data storage unit 109.

The ultrasonic diagnostic apparatus 100 is also provided with a tomographic volume data generation unit 114 configured to generate tomographic volume data by performing 3-dimensional coordinate conversion based on the position at which the 2-dimensional tomographic image constructed in the 2-dimensional tomographic image construction unit 113 is acquired, and a 3-dimensional tomographic image construction unit 115 configured to construct a 3-dimensional tomographic image by performing volume rendering based on the luminance and opacity of tomographic volume data.

Further, a 2-dimensional elastic image construction unit 116 constructs a 2-dimensional elastic image on the basis of the plural sets of RF signal frame data stored in the data storage unit 109. An elastic volume data generation unit 117 performs 3-dimensional coordinate conversion based on the position at which the 2-dimensional elastic image constructed in the 2-dimensional elastic image construction unit 116 is acquired, and generates elastic volume data. A 3-dimensional elastic image construction unit 118 performs volume rendering based on the elasticity value and opacity of the elastic volume data generated in the elastic volume data generation unit 117, and constructs a 3-dimensional elastic image. The 3-dimensional tomographic image construction unit 115 and the 3-dimensional elastic image construction unit 118 include a function to perform 3-dimensional display using plural cross-sections of MPR (Multiple Planar Reformat), multi-slice, etc.

A synthesis processing unit 119 synthesizes a 2-dimensional tomographic image and a 2-dimensional elastic image or 3-dimensional tomographic image and a 3-dimensional elastic image according to the command from the control unit 103, and makes the synthesized image or a 2-dimensional tomographic image, etc. displayed on a display unit 120. Also, the ultrasonic diagnostic apparatus 100 is provided with a control unit 103 configured to control the above-described respective components and an operation unit 104 configured to input various information to the control unit 103. The operation unit 104 comprises devices such as a keyboard or a trackball.

The 2-dimensional tomographic image construction unit 113 inputs the RF signal frame data output from the data storage unit 109 based on the setting condition which is set by the control unit 103 to perform signal processing such as gain compensation, log compression, detection, edge enhancement and filtering, and constructs a 2-dimensional tomographic image.

The ultrasonic probe 102 is capable of measuring transmission/reception directions ($\theta$, $\Phi$) at the same time as transmitting and receiving ultrasonic waves. Here, $\theta$ is the beam angle of the ultrasonic beam along the scan plane, and $\Phi$ is the swing angle in the minor-axis direction. The volume data generation unit 114 performs 3-dimensional conversion on plural 2-dimensional tomographic images based on the transmission/reception directions ($\theta$, $\Phi$) which is equivalent to the positions at which the 2-dimensional tomographic images are acquired, and generates tomographic volume data. The 3-dimensional tomographic image construction unit 115 performs volume rendering using the following equations (1)~(3) for constructing a 3-dimensional tomographic image from the tomographic volume data.

$$C\text{out}(i) = C\text{out}(i-1) + (1 - A\text{out}(i-1)) \cdot A(i) \cdot C(i) \cdot S(i) \quad (1)$$

$$A\text{out}(i) = A\text{out}(i-1) + (1 - A\text{out}(i-1)) \cdot A(i) \quad (2)$$

$$A(i) = \text{Opacity}[C(i)] \quad (3)$$

Here, C(i) is the luminance value of the i-th voxel on the line of sight, in the case that a 3-dimensional tomographic image is viewed from a certain point on a created 2-dimensional projection plane. Cout(i) is the output pixel value. For example, when the luminance values of N-number of voxels are lined on a line of sight, luminance value Cout(N−1) in which the luminance values up to the voxel which is i=0~N−1 are integrated becomes the ultimate output pixel value. Cout(i−1) indicates the integrated value up to the (i−1)-th voxel.

Also, A(i) is the opacity of the i-th luminance value that exists on the line of sight, and is the tomographic opacity table in values of 0~1.0 as shown in the equation (3). The tomographic opacity table determines the contribution ratio to the 2-dimensional projection plane (3-dimensional tomographic image) to be output by referring to the opacity from the luminance value.

S(i) is the weighting component for shading which is calculated by the gradient acquired by luminance value C(i) and the surrounding pixels values thereof. For example, 1.0 is given to S(i) for maximum reflection when the light source coincides with the normal line of the plane that centers around voxel "i" and 0.0 is given to S(i) when the light source and the normal line are orthogonal to each other, for indicating accentuation effect.

Both Cout (i) and Aout (i) have 0 as the initial value. As shown in the equation (2), Aout(i) is integrated each time it passes through a voxel and converged to 1.0. Thus as shown in the above equation (1), when integrated value Aout(i−1) of up to the (i−1)-th opacity is about 1.0, the i-th and sequence luminance values C(i) will not be reflected on the output image.

The 2-dimensional elastic image constructing unit 116 measures the displacement from the plural sets of RF signal frame data stored in the data storage unit 109. Then the 2-dimensional elastic image constructing unit 116 calculates the elasticity value on the basis of the measured displacement, and constructs a 2-dimensional elastic image. The elasticity value is any of the elastic information such as the strain, elasticity modulus, displacement, viscosity, and strain factor. The elastic volume data generating unit 117 executes the 3-dimensional conversion on plural 2-dimensional elastic images on the basis of the transmitting/receiving directions (θ, Φ) equivalent to the obtained position of the 2-dimensional image, and generates the elastic volume data. The 3-dimensional elastic image construction unit 118 performs volume rendering on the elastic volume data on the basis of the elasticity value, and constructs a 3-dimensional elastic image.

The configuration of characteristic parts in the present example will be described below. As shown in FIG. 1, a noise frame interpolation unit 121 is provided in association with the elastic volume data generation unit 117 in the present example. Also, though not shown in the diagram, a swing device for swinging the ultrasonic probe 102 in the minor-axis direction is attached to the ultrasonic probe 102. Via the swing device, a swing control unit 110 configured to control swing angle Φ of a scan plane of the ultrasonic 102 is provided. From the swing control unit 110, swing angle Φ of the ultrasonic probe 102 is input to the control unit 103.

Figure 2:
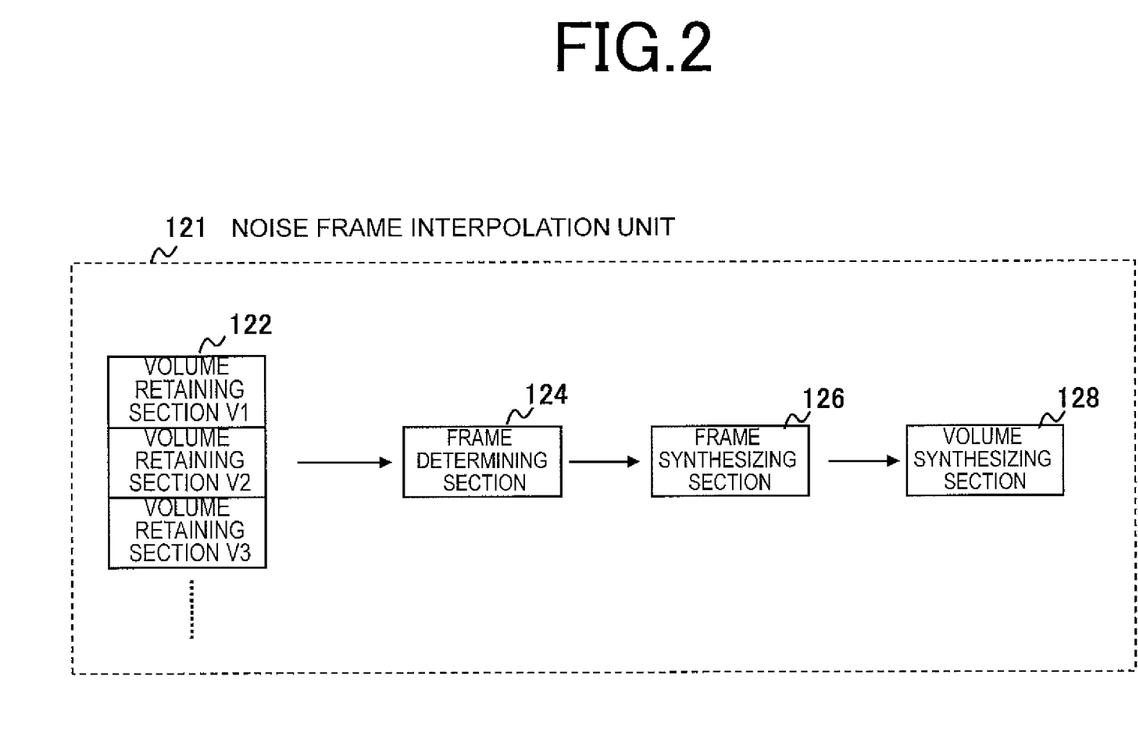
FIG. 2 is a block diagram showing detailed configuration of a noise frame interpolation unit which is the feature of the first example in FIG. 1.

The noise frame interpolation unit 121 is configured as shown in the block diagram of FIG. 2. The elastic volume data sets that are sequentially generated by the elastic volume data generation unit 117 are accumulated in volume retaining sections V1, V2, V3, . . . of a volume retaining section 122 as consecutive plural sets of elastic frame data in the minor-axis direction. The noise frame interpolation unit 121 is configured including a frame determination section 124 configured to sequentially read out the elastic frame data sets from the volume retaining section 122 and determine the adequacy in image quality of the elastic frame data, a frame synthesizing section 126 configured to synthesize the elastic frame data sets considering the determination result in the frame determination section 124, and a volume synthesizing section 128 configured to generate the elastic volume data using the elastic frame data which is synthesized in the frame synthesizing section 126.

Here, a noise frame will be described. A noise frame is referred to an elastic frame which is incapable of reflecting the information on an adequate hardness, such as the elastic frame in which an elasticity value could not be obtained since the pressure was so rough that it surpassed the displacement detection range or the elastic frame in which the compression and tension are mixed with respect to the arithmetic direction of the elasticity value (for example, strain in the depth direction). When such noise frame is included in elasticity volume data, it is likely that noise will be generated in a 3-dimensional elastic image which increases inaccuracy in diagnosis. Given this factor, the present example is characterized in comprising the noise frame interpolation unit 121 capable of removing influence of a noise frame for generating high quality 3-dimensional elastic images. The processing procedure of the noise frame interpolation unit 121 will be described below in several examples.

EXAMPLE 1

The method for noise frame interpolation in the first example will be described referring to FIG. 3. As shown in FIG. 3(a), elastic volume data formed by plural sets of elastic frame data is acquired by swinging the ultrasonic probe in the minor-axis direction, and stored in the volume retaining section 122. As shown in FIG. 3(b), the plural sets of elastic frame data that form the elastic volume data to be acquired will be synthesized in the frame synthesizing section 126, and elastic volume data formed by the synthesized plural sets of elastic frame data is further generated in the volume synthesizing section 128. The synthesized elastic frame data sets are set, for example as synthesized elastic frame data 302 (Φ2) by averaging and synthesizing consecutive three sets of elastic frame data (1Φ, 2Φ, 3Φ)) 301 as shown in FIG. 3(c). In the same manner, consecutive three sets of elastic frame data (Φ2, Φ3, Φ4) 301 are averaged and synthesized, and set as synthesized elastic frame data 303 (Φ3).

Figure 3:
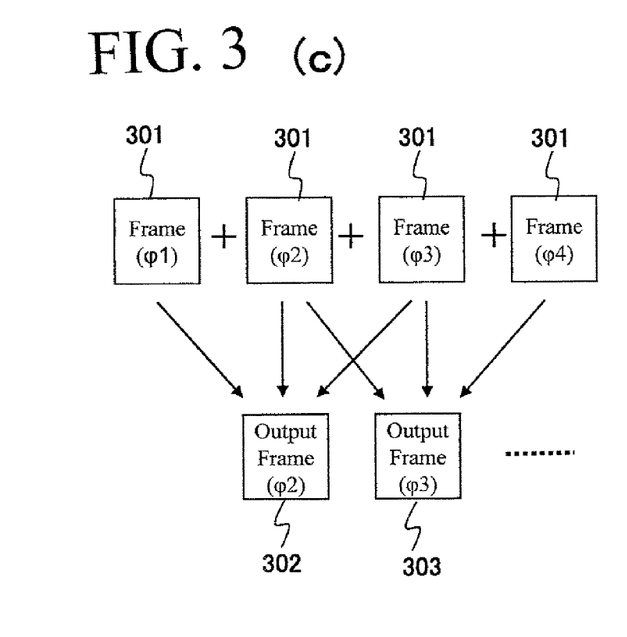
FIGS. 3A and 3B show the processing procedure of the first example regarding a noise frame interpolation unit in the present invention.
FIG. 3C is a schematic of the processing procedure illustrated in Fins. 3A and 3B.

As for the averaging method for synthesis in FIG. 3(c), either one of an FIR filter (finite impulse response filter) or an IIR filter (infinite impulse response filter) can be used. In accordance with the volume of a memory region, the number of stages in the FIR filter (in the case that 5 pieces of filters are used: about [1 mm] of precision) or the IIR filter can be adjusted. By repeating the synthesizing process of frames shown in FIG. 3 (c), elastic volume data is generated.

In accordance with the first example, elastic volume data is generated by replacing the respective sets of elastic frame data that form elastic volume data with the synthesized elastic frame data in which the adjacent plural sets of elastic frame data are synthesized, the synthesized elastic frame data sets that form the elastic volume data become the averaged data of the adjacent plural sets of the elastic frame data. Moreover, each of the adjacent plural sets of elastic frame data also become the averaged adjacent plural sets of elastic frame data as well, thus the present example can improve the continuity of image quality in the minor-axis direction of the plural sets of elastic frame data that form elastic volume data.

Also, in accordance with the present example, for example, even when a noise is included in one piece of elastic frame data, the influence of noise can be reduced by synthesizing adjacent plural sets of elastic frame data of good quality and smoothing with a high-quality image. In other words, even in the case that the continuity in the minor-axis direction is lost due to the influence of a noise frame at the time of generating volume data, elastic volume data with high continuity can be constructed by removing the influence of the noise. As a result, it is possible to obtain stable 3-dimensional elastic images.

EXAMPLE 2

Figure 4:
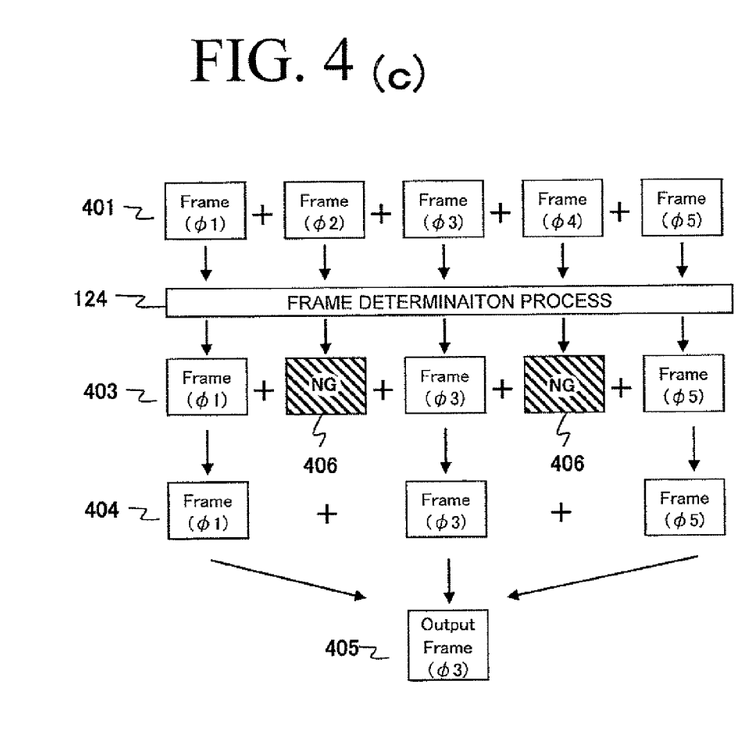
FIGS. 4A and 4B show the processing procedure of a second example regarding a noise frame interpolation unit in the present invention.
FIG. 4C is a schematic of the processing procedure illustrated in FIGS. 4A and 4B.

The method for noise frame interpolation in the second example will be described referring to FIG. 4. As shown in FIG. 4(a), the elastic volume data formed by plural sets of elastic frame data is obtained by swinging the ultrasonic probe in the minor-axis direction, and stored in the volume retaining section 122. The difference between the second example and the first example is that, as shown in FIG. 4(c), the adequacy of each image quality in elastic frame data sets (Φ1, Φ2, . . . ) 401 that are sequentially stored in the volume retaining section 122 is determined in a frame determining section 124. As a result of the determination made in the frame determining section 124, it is assumed that the image quality of elastic frame data (Φ1, Φ3, Φ5) 403 is determined as adequate and the image quality of elastic frame data (Φ2, Φ4) 406 is determined as inadequate, i.e. a noise frame. In this case, the frame synthesizing section 126 of the present example removes the elastic frame data (Φ2, Φ4) 406 which is determined as a noise frame, averages the remaining three sets of elastic frame data (Φ1, Φ3, Φ5) 404, and outputs the averaged data to the volume synthesizing section 128 as synthesized elastic frame data (Φ3) 405.

The algorithm of the frame determination section 124 will be described. A commonly-known method can be adapted to the method for determining the adequacy of image quality in one set of elastic frame data. For example, correlation coefficient which indicates the coincidence of images, the average of elastic frames (displacement, strain, strain ratio, or elasticity modulus), deviation or S/N (noise ratio), etc. is set as an evaluation value, and determination is to be made whether or not the evaluation value satisfies a determination threshold hold value. The equation (4) for calculating strain deviation SD will be described below. The frame with large amount of noise has great variability with respect to the average, thus the adequacy of image quality can be determined.

$$SD = \frac{\sum_{i=0}^{W} \sum_{j=0}^{H} (d(i,j) - \bar{d})^2}{W * H} \quad (4)$$

W: image width

H: image height d(i, j): strain data $\bar{d}$: averaged strain data

Therefore, in accordance with the second example, plural sets of elastic frame data are synthesized by removing the noise frame, thus it is possible to further improve the continuity of image quality in the minor-axis direction regarding the plural sets of elastic frame data that form elastic volume data compared to the first example.

EXAMPLE 3

Figure 5:
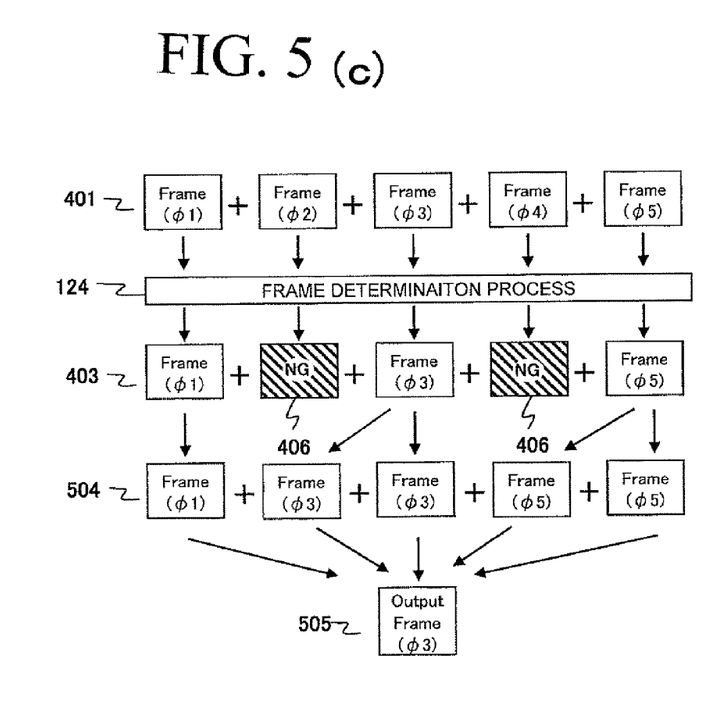
FIGS. 5A and 5B show the processing procedure of a third example regarding a noise frame interpolation unit in the present invention.
FIG. 5C is a schematic of the processing procedure illustrated in FIGS. 5A and 5B.

The method for noise frame interpolation in the third example will be described referring to FIG. 5. As shown in FIG. 5(a), the elastic volume data formed by plural elastic frame data sets is obtained by swinging the ultrasonic probe in the minor-axis direction, and stored in the volume retaining section 122. The difference in the third example from the second example is that the elastic frame data (φ2, φ4) 406 which is removed as a noise frame is replaced by the copy of elastic frame data (φ3, φ5) which follows the elastic frame data (φ2, φ4) 406. In this manner, in accordance with the present third example, five sets of elastic frame data (φ1, φ3, φ3, φ5, φ5) 504 are averaged and output to the volume synthesizing section 128 as a set of synthetic elastic frame data (φ3) 505.

In accordance with the present third example, a synthesized frame can be created by constantly fixing the number of frames in elastic frame data related to the synthesis processing, as compared to the second example.

EXAMPLE 4

Figure 6:
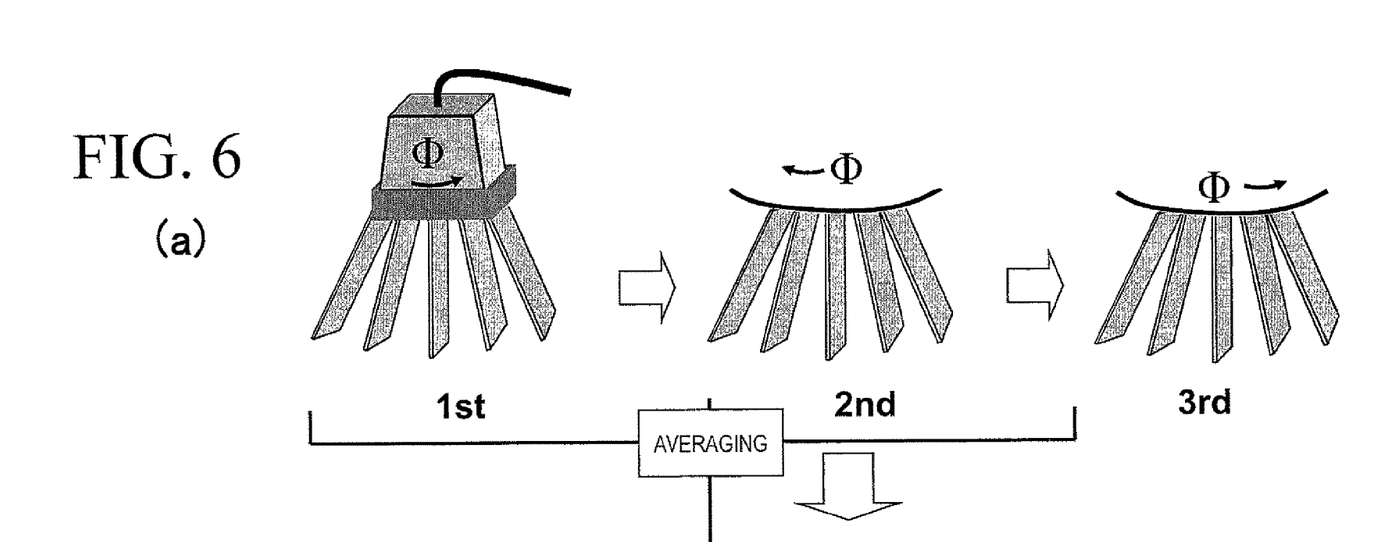
FIGS. 6A and 6B show the processing procedure of a fourth example regarding a noise frame interpolation unit in the present invention.

The noise frame interpolation method of the fourth example will be described referring to FIG. 6. In the first~third examples, one set of synthetic frame data is created using consecutive adjacent plural sets of elastic frame data, while focusing on creating consecutive and stable elastic frame data sets within one set of elastic volume data.

On the other hand, as shown in FIG. 6(a), the present fourth example stores plural sets of elastic volume data (three sets in the diagram) in the volume retaining section 122 by repeating the operation to obtain the elastic volume data formed by plural sets of elastic frame data while swinging the ultrasonic probe in the minor-axis direction and store the obtained volume data in the volume retaining section 122.

Then in the present example, the frame synthesizing section 126 takes out the plural sets of elastic frame data of which the swing angle positions correspond to each other from among the plural sets of elastic volume data obtained by plural times of volume scanning performed at different times and averages the taken out data sets, so as to generate the synthetic elastic frame data in the swing angle position (minor-axis position) as shown in FIG. 6(b). It means, in the present example, the plural sets of elastic frame data corresponding to the same minor-axis position in the respective elastic volume sets are synthesized in the frame synthesizing section B126. The synthesized elastic frame data is set as the synthetic elastic frame data at the corresponding minor-axis positions among the elastic volume data sets. In this manner, one set of elastic volume data can be created by repeating the synthesis processing of elastic frame data sets in each set of elastic volume data by the number of frames in the minor-axis direction.

Here, in order to synthesize the elastic frame data sets in the same swing-angle positions in the respective elastic volume data sets without positional displacement, the present example detects swing angle Φ of the ultrasonic probe 102 in the swing control unit 110, and outputs the detected swing angle Φ to the control unit 103. The control unit 103 controls transmission and reception of the ultrasonic probe 102 via the transmission/reception control unit 107 on the basis of swing angle Φ. Also, the RF frame data and swing angle Φ are stored at the same time in the data storage unit 109. In this manner, swing angle Φ is appended to the elastic frame data sets to be collected in the elastic volume data generation unit 117 so that the swing angles Φ in the plural sets of elastic volume data can be corresponded to each other.

Compared to the first~third examples, the present example synthesizes the elastic frame data sets that are at the positions corresponding to the same swing angle Φ in the respective elastic volume data sets, thus positional displacement in the minor-axis direction does not need to be taken into consideration. However, compared to the first~third examples, temporal displacements can occur since plural sets of elastic volume data are collected, thus the present example has a disadvantage in that image quality needs to be lowered in order to improve the real-time efficiency.

EXAMPLE 5

Figure 7A:
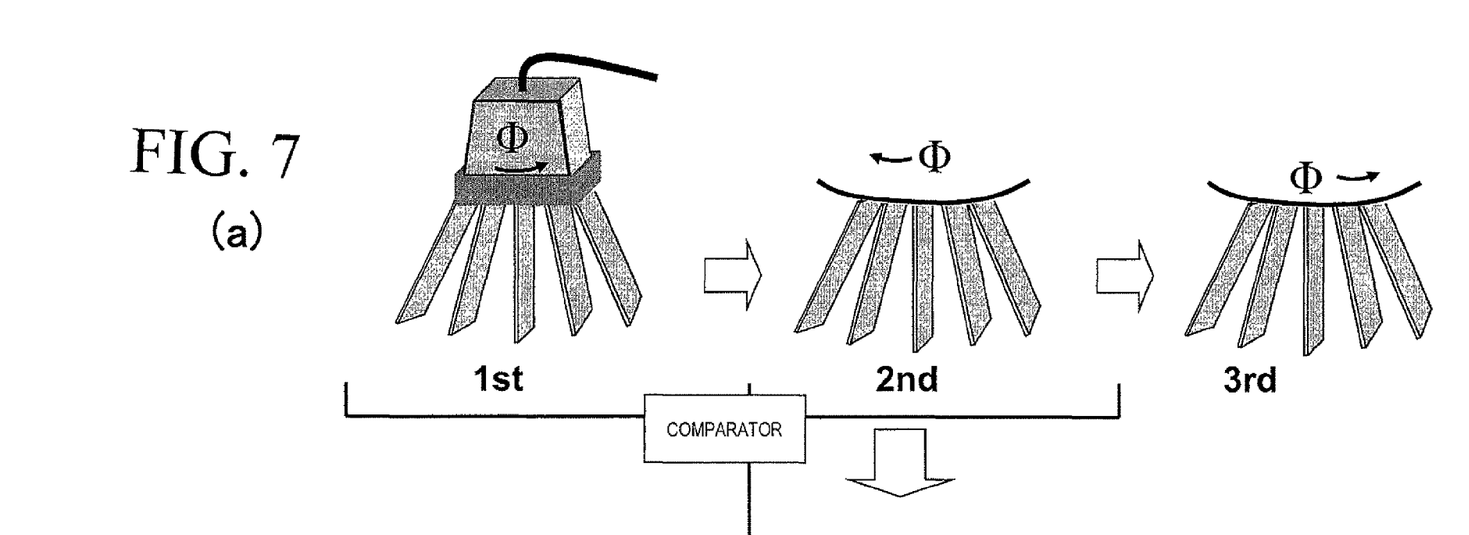
FIGS. 7A and 7B show the processing procedure of a fifth example regarding a noise frame interpolation unit in the present invention.
Figure 7B:
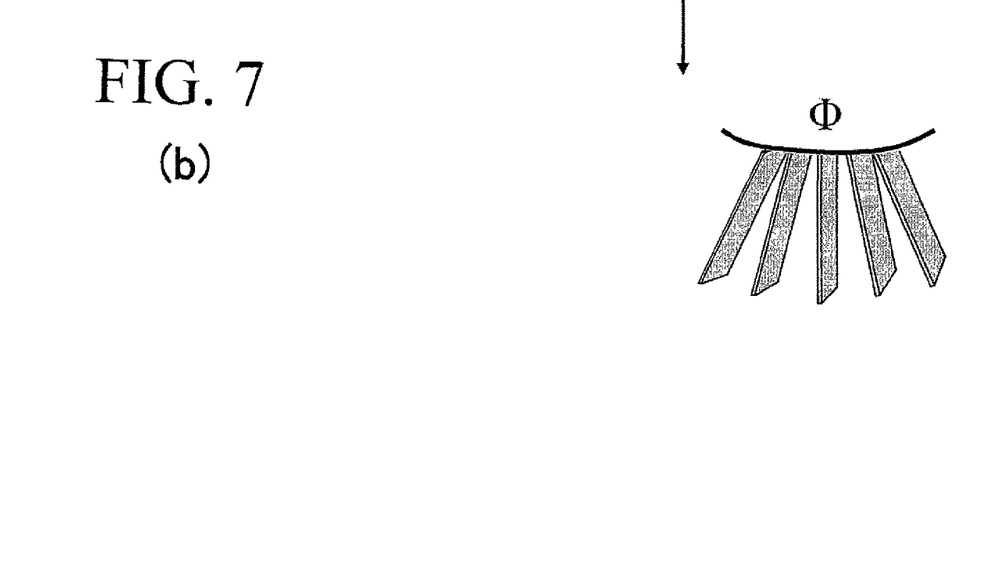

The noise frame interpolation method in the fifth example will be described referring to FIG. 7. As in the fourth example, plural sets of elastic volume data are collected, then elastic volume data sets of high quality are consecutively and stably generated. As shown in FIG. 7, the difference between the present example and the fourth example is that elastic volume data is formed by comparing the image qualities of elastic frame data sets at the swing angle positions in which, for example three sets of elastic volume data sets are corresponded to each other, selecting the elastic frame data of the best image quality, and synthesizing the elastic frame data sets having the best image quality in each swing angle.

More specifically, the three sets of elastic volume data are retained in the volume retaining section 122, and the adequacy of the image qualities in the elastic frame data sets of the corresponding swing angles in the respective stored elastic volume data are determined by the frame determining section 124. On the basis of the determination result, the elastic frame data set having the best image quality is selected in the frame synthesizing section 126 from among the elastic frame data sets of the corresponding swing angle. Then as shown in FIG. 7(b), the volume synthesizing section 128 generates elastic volume data which is the collection of the elastic frame data sets having the best image quality at the respective swing-angle positions.

EXAMPLE 6

The noise frame interpolation method in the sixth example will be described referring to FIG. 8. The present example is the combination of the synthesizing process of the elastic frame data sets in one set of elastic volume data described in the first~third examples and the synthesizing process of the elastic frame data sets among plural sets of elastic volume data described in the fourth and fifth examples. In this manner, it is possible to generate elastic volume data which is further improved in stability and image quality.

Figure 8:
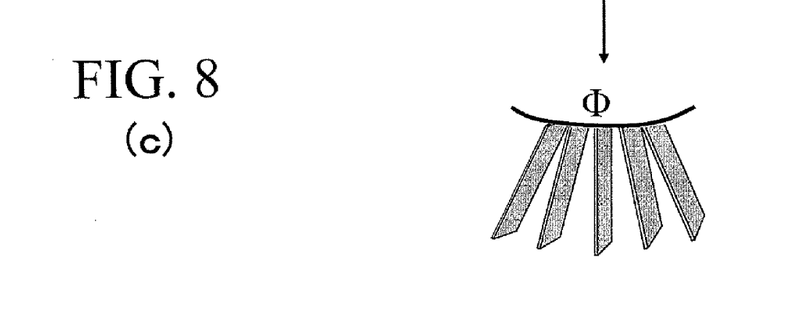
FIGS. 8A, 8B and 8C show the processing procedure of a sixth example regarding a noise frame interpolation unit in the present invention.

More specifically, as shown in FIG. 8(a), plural sets of elastic volume data formed by plural sets of elastic frame data are obtained by swinging the ultrasonic probe in the minor-axis direction and sequentially stored in the volume retaining section 122. As shown in FIG. 8, the frame synthesizing section 126 synthesizes the adjacent plural sets of elastic frame data in each set of obtained plural sets of elastic volume data, and generates plural sets of elastic volume data in which the synthesized elastic frame data sets are collected. These generated plural sets of elastic volume data are retained in the volume data retaining section 122 again.

Further, for example as shown in FIG. 8(c), the volume synthesizing section 128 averages the synthesized elastic frame data sets, for example at the same swing positions or selects the synthesized elastic frame data having the best image quality from among plural sets of the elastic volume data, and generates the elastic volume data formed by new sets of synthesized elastic frame data sets. In this manner, the present example is capable of consecutively displaying images as moving images by retaining volume data sets while sliding them by one volume in the volume retaining section 122 and further improving its efficiency. The present embodiment can combine the synthesizing process by frame determination, i.e. determining adequacy of image quality at the time of synthesizing plural sets of elastic frame data and the synthesizing process by frame determination at the time of synthesizing elastic volume data sets.

EXAMPLE 7

Figure 9:
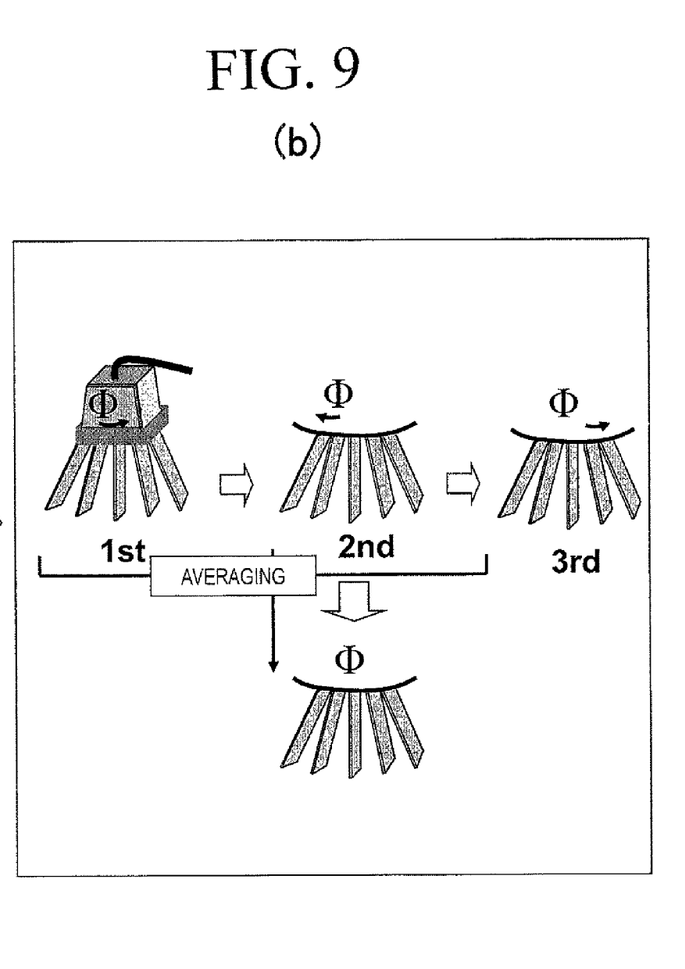
FIGS. 9A and 9B show the processing procedure of a seventh example regarding a noise frame interpolation unit in the present invention.

The noise frame interpolation method in the seventh example will be described referring to FIG. 9. Generally, high-quality ultrasonic images are obtained using an ultrasonic diagnostic apparatus by scanning ultrasonic beams in the major-axis direction with a dense pitch. Also, in order to obtain high-quality 3-dimensional ultrasonic images, the swinging of transducers need to be performed with a dense frame pitch in the minor-axis direction. However, image quality and real-time efficiency are in a trade-off relationship, thus the dense frame pitch is to be set in the high-definition 3-dimensional mode, and a rough frame pitch is set in the real-time 3-dimensional mode.

As shown in FIG. 9(a), since a dense frame pitch in the minor-axis direction is set in the case of high-definition 3-dimensional mode, it is suitable that the synthesizing process is performed among the adjacent plural sets of elastic frame data within one set of elastic volume data as described in the first~third examples. That is, the swing angle positions in the adjacent plural sets of elastic frame data are assumed to be about the same. On the other hand, since a rough frame pitch is set in the case of the real-time 3-dimensional mode as shown in FIG. 9(b), when the synthesizing process is performed among the plural sets of elastic frame data as described in the first~third examples, generation of a large displacement occurs in the swing-angle positions of the adjacent plural sets of elastic frame data which lowers image quality of the synthesized elastic frame data. Therefore, in the case of real-time 3-dimensional mode, it is preferable to interpolate the elastic frame data sets of low image quality by performing synthesizing process using the plural sets of elastic frame data at the same swing angle positions among the plural sets of elastic volume data as described in the fourth and the fifth examples.

Given this factor, the present example is provided with a synthesizing method switching section configured to detect the pitch of the swing angle in plural sets of elastic frame data that form the elastic volume data and switch the high-definition 3-dimensional mode and the real-time 3-dimensional mode in accordance with the detected pitch. More specifically, the synthesizing method switching section generates elastic volume data in the high-definition 3-dimensional mode in FIG. 9(a) when the detected pitch of the swing angle is smaller than a set value. Then when the detected pitch of the swing angle is the set pitch or greater, elastic volume data is generated by the real-time 3-dimensional mode in FIG. 9(b). As for the set value of the detected pitch of the swing angle for switching the synthesizing methods, for example, the high-definition 3-dimensional mode is used when the frame pitch corresponding to the swing angle pitch is 0.05 [mm], and the real-time 3-dimensional mode is used when the frame pitch is 1 [mm].

In addition, in accordance with the switching of the high-definition 3-dimensional mode and the real-time 3-dimensional mode, a mode switching command can be output from the noise frame interpolation section 121 or the control unit 103 to the transmission/reception control unit 107. According to the output command, the transmission/reception control unit 107 is capable of controlling the density of the ultrasonic-wave pitch in the major-axis direction to be dense for the high-definition 3-dimensional mode and rough for the real-time 3-dimensional mode.

In accordance with the present example, the interpolation process of noise frames is automatically performed according to the high-definition 3-dimensional mode or the real-time 3-dimensional mode, thus the usability of the apparatus can be improved.

As mentioned above, a first embodiment of the present invention, in the 3-dimensional elastic image generation method which generates a 3-dimensional elastic image by volume rendering elastic volume data formed by the plural sets of elastic frame data obtained regarding the object 101, with respect to the elastic frame data sets that form the elastic volume data, synthesizes the plural sets of elastic frame data that are adjacent in the swing-direction including the relevant elastic frame data sets, and generates elastic volume data by the synthesized plural sets of elastic frame data.

Also, in the ultrasonic diagnostic apparatus comprising the elastic volume data generating unit 117 configured to collect the plural sets of elastic volume data obtained by swinging the scan plane of the ultrasonic wave to be transmitted to the object 101 in the direction which intersects with the scan plane so as to generate elastic volume data and the 3-dimensional elastic image constructing unit 118 configured to construct a 3-dimensional elastic image on the basis of the elastic volume data generated by the elastic volume data generating unit 117, wherein the elastic volume data generating unit 117 creates synthetic elastic frame data by synthesizing the plural sets of elastic frame data that are adjacent in the swing direction, and generates the elastic volume data on the basis of the synthetic elastic frame data.

The present embodiment is characterized in the method for generating elastic volume data. In concrete terms, elastic volume data is generated by replacing the respective sets of elastic frame data that form the elastic volume data with the elastic frame data in which adjacent plural sets of elastic frame data are synthesized. In this manner, the synthetic elastic frame data sets that form the elastic volume data become the averaged data of adjacent plural sets of elastic frame data. Moreover, each of the adjacent plural sets of elastic frame data is also the averaged data of the adjacent plural sets of elastic frame data respectively, thus the continuity of image quality in the minor-axis direction of the plural sets of elastic frame data that form the elastic volume data can be improved. For example, even when a noise is included in a set of elastic frame data, the influence of the noise can be suppressed by synthesizing the adjacent plural sets of high-quality elastic frame data. In other words, even in the case that the continuity in the minor-axis direction is lost at the time of creating volume data due to a noise frame, it is possible to construct volume data with high continuity by removing the influence of the noise.

In this case, the synthesizing process for generating synthetic elastic frame data can be performed by averaging the plural sets of elastic frame data that are adjacent in the swing direction including the relevant elastic frame data. Also instead, synthetic elastic frame data can be generated by determining the adequacy of image quality in each set of elastic frame data and removing the elastic frame data which is determined as having inadequate image quality. Further, the present embodiment is capable of generating synthetic elastic frame data by determining the adequacy of image quality in each set of elastic frame data and replacing the elastic frame data which is determined as having inadequate image quality with one or the average of two sets of elastic frame data that are adjacent to the relevant elastic frame data.

Also, in order to achieve the previously mentioned objective, in the 3-dimensional elastic image generation method for generating a 3-dimensional elastic image by volume rendering on the basis of elastic volume data formed by plural sets of elastic frame data regarding an object, a second embodiment of the present invention stores plural sets of the elastic volume data, generates synthetic elastic frame data based on the plural sets of elastic frame data in the corresponding swing angle positions in the stored plural sets of elastic volume data, and generates elastic volume data on the basis of the synthetic elastic frame data.

Also, in the ultrasonic diagnostic apparatus comprising the elastic volume data generating unit 117 configured to collect plural sets of elastic volume data obtained by swinging the scan plane of the ultrasonic wave to be transmitted to the object 101 in the direction which intersects with the scan plane so as to generates elastic volume data and the 3-dimensional elastic image constructing unit 118 configured to construct a 3-dimensional elastic image on the basis of the elastic volume data generated by the elastic volume data generating unit 117, the elastic volume data generating unit 117 stores plural sets of elastic volume data, generates synthetic elastic frame data based on the plural sets of elastic frame data in the corresponding swing angle positions in the stored plural sets of elastic volume data, and generates elastic volume data on the basis of the synthetic elastic frame data sets.

In the first embodiment, each set of synthetic elastic frame data is generated by synthesizing consecutive plural sets of elastic frame data within one set of elastic volume data and displacing the plural sets of elastic frame data to be synthesized by every set. On the other hand, the second embodiment is different in generating elastic volume data that the plural sets of elastic volume data obtained in the same region in an object are stored and plural sets of elastic frame data in which the swing angle positions in the minor-axis direction among the stored plural sets of elastic volume data are synthesized. In this manner, as in the first embodiment, the continuity of image quality can be improved in the minor-axis direction of plural sets of elastic frame data that form the elastic volume data. In particular, the second embodiment is effective in the case that the pitch is rough in the minor-axis direction of plural sets of elastic frame data. On the contrary, the first embodiment is more effective to be used in the case that the pitch in the minor-axis direction is dense, since the plural sets of elastic frame data having different swing angle positions are to be synthesized.

In this case, the synthesizing process for generating synthetic elastic frame data can be performed by averaging the plural sets of elastic frame data in the corresponding swing angle positions. Also, the synthesizing process can set the synthetic elastic frame data having the highest image quality from among the plural sets of elastic frame data in the corresponding swing angle positions as synthetic elastic frame data.

Further, by combining these synthesizing processes, the present embodiment can store plural sets of elastic volume data, generate new elastic frame data sets on the basis of the plural sets of synthetic elastic frame data in the corresponding swing angle positions in the stored plural sets of elastic volume data, generate new elastic volume data on the basis of the newly generated synthetic elastic frame data sets, and generate a 3-dimensional elastic image based on the newly generated elastic volume data.

In this case, the synthesizing process of new synthetic elastic frame data can be performed by averaging the plural sets of synthetic elastic frame data in the corresponding swing angle positions. Also, the synthesizing process of new synthetic elastic frame data can be performed by setting the elastic frame data having the best image quality from among the plural sets of synthetic elastic frame data at the corresponding swing positions.

Further, in the 3-dimensional elastic image generation method which generates a 3-dimensional elastic image by volume rendering on the basis of elastic volume data formed by the plural sets of elastic frame data that are obtained regarding an object, with respect to the respective sets of elastic frame data that form elastic volume data, a third embodiment of the present invention detects a first synthesizing process which creates synthetic elastic frame data by synthesizing the plural sets of elastic frame data that are adjacent in the swing direction including the relevant elastic frame data so as to generate the elastic volume data in which the respective elastic frame data sets are replaced with the synthetic elastic frame data, a second synthesizing process which stores plural sets of elastic volume data and generates the synthetic elastic frame data sets based on the plural sets of elastic frame data in the corresponding swing angle positions of the stored plural sets of elastic volume data and generates the elastic volume data on the basis of the synthetic elastic frame data sets, and the pitch in the swing direction of the plural sets of elastic frame data that form the elastic volume data, so that elastic volume data is generated by the first synthesizing process when the detected pitch is smaller than a set value and elastic volume data is generated by the second synthesizing process when the detected pitch is the set value or greater, then generates a 3-dimensional elastic image on the basis of the generated elastic volume data.

In other words, the third embodiment of the present invention is the combination of advantages in the first and second synthesizing processes. As previously described, in the case that the pitch in plural sets of elastic frame data in the minor-axis direction is dense (for example, high-definition 3-dimensional mode), even when the synthesizing process is performed using adjacent plural sets of elastic frame data in the same elastic volume data, the displacement of the swinging angle in the minor-axis direction can be ignored, thus high-quality elastic volume data can be generated. On the other hand, it is preferable to perform the synthesizing process of plural sets of elastic frame data in the corresponding swing-angle positions among plural sets of elastic volume data, since the displacement of the swing angle in the minor-axis cannot be ignored in the case that the pitch of plural sets of elastic frame data in the minor-axis direction is rough (for example, real-time 3-dimensional mode).

In the third embodiment, the first synthesizing process and the second synthesizing process can apply the synthesizing process of the first embodiment and the second embodiment respectively.

The ultrasonic diagnostic apparatus for executing the 3-dimensional elastic image generation method of the above-described first~third embodiments comprises an elastic volume data generating unit configured to generate elastic volume data by collecting the plural sets of elastic frame data obtained by swinging the scan plane of the ultrasonic signal to be transmitted to an object in the direction which is orthogonal to the scan plane, and a 3-dimensional elastic image constructing unit configured to construct a 3-dimensional elastic image on the basis of the elastic volume data generated by the elastic volume data generating unit. That is, the 3-dimensional elastic image constructing unit can construct a 3-dimensional elastic image based on the elastic volume data generated in the elastic volume data generating unit by adopting the first~third embodiments of the present invention to the elastic volume data generating unit.

DESCRIPTION OF REFERENCE NUMERALS 100 ultrasonic diagnostic apparatus
102 ultrasonic probe
103 control unit
104 operation unit
107 transmission/reception control unit
108 phasing and adding unit
109 data storage unit
110 swing control unit
116 2-dimensional elastic image constructing unit
117 elastic volume data generating unit
118 3-dimensional elastic image constructing unit
119 synthesis processing unit
120 display unit
121 noise frame interpolation unit

The invention claimed is:

1. An ultrasonic diagnostic apparatus comprising:
an ultrasonic probe configured to transmit ultrasonic waves to an object and receive reflected echo signals from the object; and
a processor configured to:
transmit electrical signals to the ultrasonic probe in accordance with swinging the ultrasonic probe in a minor axis direction of the ultrasonic probe, the electrical signals causing the ultrasonic probe to transmit ultrasonic waves to the object and receive reflected echo signals from the object;
generate a plurality of elastic frame data sets along the swing direction based on the received reflected echo signals, wherein each elastic frame data set of the plurality of elastic frame data sets is comprised of a respective frame of elastic frame data orthogonal to the swing direction;
process the plurality of elastic frame data sets by determining an adequacy of image qualities of each respective frame of elastic frame data and replacing each respective frame of elastic frame data determined to be inadequate with a copy of an adequate frame of elastic frame data which is adjacent to the respective inadequate frame in the swing direction of the ultrasonic probe;
generate a plurality of synthesized elastic frame data sets wherein each respective synthesized elastic frame data set is generated by averaging a respective subset of the processed plurality of elastic frame data sets localized to the respective synthesized elastic frame data set;
generate elastic volume data based on the generated plurality of synthesized elastic frame data sets;
construct a 3-dimensional elastic image based on the generated elastic volume data; and
output the constructed 3-dimensional elastic image.

2. The ultrasonic diagnostic apparatus according to claim 1, wherein the processor is further configured to generate the copy of the adequate frame by averaging two sets of the plurality of elastic frame data sets that are adjacent to the inadequate elastic frame.

3. The ultrasonic diagnostic apparatus according to claim 1, wherein the plurality of synthetic elastic frame data sets are data sets having the best image quality among the plurality of elastic frame data sets at the corresponding swing-angle positions.

4. The ultrasonic diagnostic apparatus according to claim 1, wherein the processor is further configured to:
store the plurality of elastic volume data sets,
generate new sets of synthetic elastic frame data based on the plurality of synthetic elastic frame data sets in the corresponding swing-angle positions among the stored plurality of elastic volume data sets;
generate a new set of elastic volume data based on the newly generated synthetic elastic frame data sets; and
construct a 3-dimensional elastic image based on the newly generated elastic volume data.

5. The ultrasonic diagnostic apparatus according to claim 4, wherein the new sets of synthetic elastic frame data are the data sets having the best image quality among the plurality of synthetic elastic frame data sets in the corresponding swing angle positions.

6. The ultrasonic diagnostic apparatus according to claim 1, wherein the processor is further configured to:
detect, with respect to each set of the plurality of elastic frame data sets, a first synthesizing process which creates synthetic elastic frame data by synthesizing the plurality of elastic frame data sets that are adjacent in the swing direction, and generates a plurality of elastic volume data sets in which each set of the plurality of elastic frame data sets are replaced with the plurality of synthesized elastic frame data sets, a second synthesizing process which stores the plurality of the elastic volume data sets and generates the plurality of synthetic elastic frame data sets based on the plurality elastic frame data sets in the corresponding swing-angle positions among the stored plurality of elastic volume data sets so as to generate the plurality of elastic volume data sets based on the generated plurality of synthesized elastic frame data sets, and a pitch in the swing direction of the plurality of elastic frame data sets that form the elastic volume data, so that the plurality of elastic volume data sets are generated by the first synthesizing process when a detected pitch is smaller than a set value and the plurality of elastic volume data sets are generated by the second synthesizing process when the detected pitch is the set value or greater, and
construct a 3-dimensional elastic image based on the generated plurality of elastic volume data sets.

7. The ultrasonic diagnostic apparatus according to claim 6, wherein the first synthesizing process determines the adequacy of image quality in each set of the plurality of elastic frame data sets, removes sets of the plurality of elastic frame data sets of which the image quality is determined as inadequate, and synthesizes the plurality of synthesized elastic frame data sets.

8. The ultrasonic diagnostic apparatus according to claim 6, wherein the second synthesizing process stores the plurality of elastic volume data sets, generates synthetic elastic frame data based on the plurality of elastic frame data sets in the corresponding swing-angle positions among the stored plurality of elastic volume data sets, and generates the plurality of elastic volume data sets on the basis of the plurality of synthesized elastic frame data sets.

9. A 3-dimensional elastic image generation method, comprising the steps of:
swinging an ultrasonic probe in a minor axis direction of the probe, the ultrasonic probe configured to transmit ultrasonic waves to an object and receive reflected echo signals from the object;
transmitting electrical signals to the ultrasonic probe in accordance with the swinging of the ultrasonic probe, the electrical signals causing the ultrasonic probe to transmit ultrasonic waves to the object and receive reflected echo signals from the object;
generating a plurality of elastic frame data sets along the swing direction based on the received reflected echo signals, wherein each elastic frame set of the plurality of elastic frame data sets is comprised of a respective frame of elastic frame data orthogonal to the swing direction;
processing the plurality of elastic frame data sets by determining an adequacy of image qualities of each respective frame of elastic frame data and replacing each respective frame of elastic data determined to be inadequate with a copy of an adequate frame of elastic frame data which is adjacent to the respective inadequate frame in the swing direction of the ultrasonic probe;
generating a plurality of synthesized elastic frame data sets wherein each respective synthesized elastic frame data set is generated by averaging a respective subset of the processed plurality of elastic frame data sets localized to the respective synthesized elastic frame data set;
generating elastic volume data based on the generated plurality of synthesized elastic frame data sets;
constructing a 3-dimensional elastic image based on the generated elastic volume data; and
outputting the constructed 3-dimensional elastic image.

* * * * *